United States Patent [19]

Pernot et al.

[11] Patent Number: 4,484,892
[45] Date of Patent: Nov. 27, 1984

[54] HAND-HELD PNEUMATIC IMPLEMENT FOR REMOVING DENTAL SCALE

[75] Inventors: Jacques Pernot, Vieilley; Bernard Lacour, Besançon, both of France

[73] Assignee: Micro-Mega S.A., Besançon, France

[21] Appl. No.: 374,952

[22] Filed: May 5, 1982

[30] Foreign Application Priority Data

May 6, 1981 [FR] France .............................. 81 09139
Apr. 28, 1982 [FR] France .............................. 82 07478

[51] Int. Cl.³ .............................................. A61C 3/03
[52] U.S. Cl. .................................. 433/118; 433/120; 433/122; 433/132
[58] Field of Search ............... 433/118, 119, 120, 122, 433/124, 132; 318/114

[56] References Cited

U.S. PATENT DOCUMENTS

| | | | |
|---|---|---|---|
| 842,112 | 1/1907 | Perry | 433/122 |
| 2,751,685 | 6/1956 | Sharon et al. | 433/122 |
| 3,124,878 | 3/1964 | Bodine, Jr. et al. | 433/119 |
| 4,176,454 | 12/1979 | Hatter et al. | 433/119 |
| 4,427,384 | 1/1984 | Sertich | 433/120 |

FOREIGN PATENT DOCUMENTS 613672 12/1948 United Kingdom ................ 433/122

Primary Examiner—Robert P. Swiatek
Attorney, Agent, or Firm—Robert E. Burns; Emmanuel J. Lobato; Bruce L. Adams

[57] ABSTRACT

A hand-held implement for removing dental scale provided with a rigid shaft to which is applied vibrations in a rotational or circumferential direction by a dynamically unbalanced air driven turbine. The rotor of the turbine is coupled to the shaft by a bearing and the shaft is restrained from rotating and restrained axially. Provision is made for supplying cooling water through the shaft to a dental scale removing tool mounted on a free end of the vibrated shaft.

5 Claims, 6 Drawing Figures

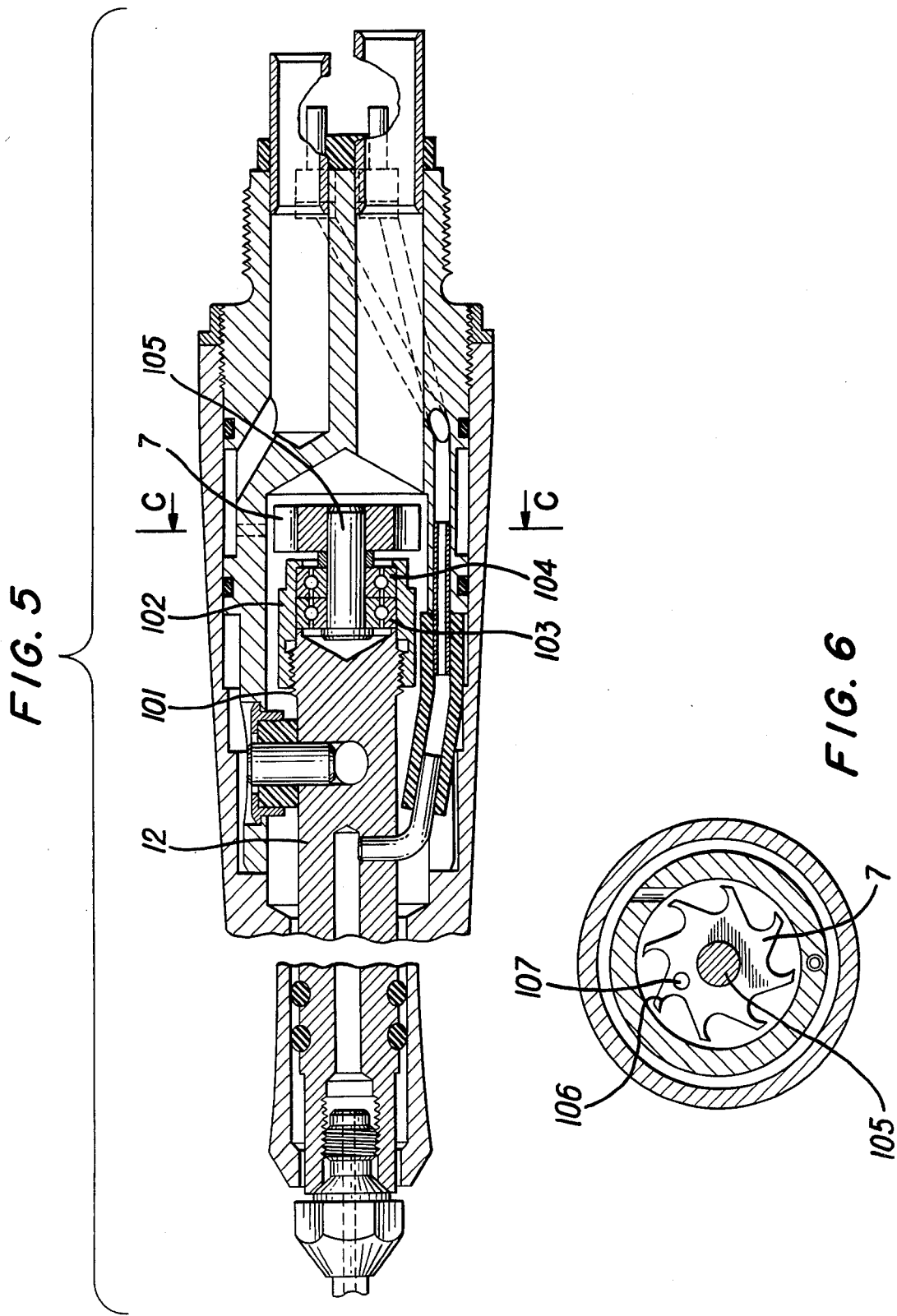

HAND-HELD PNEUMATIC IMPLEMENT FOR REMOVING DENTAL SCALE

The present invention relates to a manual pneumatic de-scaling implement for dental usage, of the type including scaler tool to which a sub-sonic vibratory movement is imparted, in which the vibratory movement is obtained by using an unbalanced mass which is driven in rotation at high speed.

De-scaling implements of this type are well known. They are used for removing the scale adhering to the enamel of healthy teeth, principally in the region of the gums. With the course of time, this scale penetrates under the gums and constitutes a refuge for bacteria, in other words areas which are the starting point of dental caries. It is consequently absolutely essential to remove this scale.

The process which is most commonly used at present consists in removing these scale deposits mechanically.

For many years this has been done manually using curettes, or scaler tools, which are operated by the dental practitioner. This method is time consuming and tedious.

In order to find an alternative to this method, it was firstly thought that causing the curettes to vibrate at ultasonic frequencies would be the answer, which does lead to a considerable saving on time and yields good results. However, it is now feared that the ultrasound may be harmful to the pulp of the teeth, and the profession has been very reserved with regard to implements employing ultrasound which have been put forward for use in this area.

Development of new products has consequently been orientated towards implements for removing scale in which the scaler tool is caused to vibrate at sub-sonic frequencies, of the order of 3000 vibrations per second.

A certain number of implements have already been put forward to this effect, but they have a complex structure, particularly in their arrangements for transmitting the vibratory movement to the scaler tool, and their assembly (and respective dis-assembly) has become considerably complicated which presents an obstacle to the everyday usage of these implements by the dental practitioner.

The present invention has the aim of overcoming these various disadvantages by providing a pneumatic de-scaling implement which is extremely simple whilst at the same time remaining very effective.

In accordance with the invention, this result is obtained by providing a hand-held pneumatic implement for removing dental scale of the type including a scaler tool to which a sub-sonic vibratory movment is imparted, in which the vibratory movement is obtained by using an unbalanced mass which is driven in rotation at high speed, and which is characterised in that the scaler tool is operated by a shaft which supports it, the shaft being unable to rotate and having its vibration produced by a compressed air turbine which is mounted on said shaft, said turbine including an out-of-balance mass or having a hole in one of its blades.

As the turbine is driven in rotation, using the compressed air, the out-of-balance mass imparts vibrations to the shaft supporting the scaler tool, and these vibrations are of a frequency which is equal to the speed of rotation of the turbine, or to a harmonic frequency thereof.

There is a danger that the friction of the special scaler tool on the enamel may bring about very rapid heating up of this area, which may reach several hundreds of degrees.

In accordance with an advantageous characteristic of carrying out the invention, the body of the pneumatic de-scaling implement in accordance with the invention includes a passage for carrying a cooling fluid to the area where the head of the scaler tool is operating.

This passage could be external or, preferably, internal, so as to thus bring the cooling fluid directly to the point of action of the head of the scaler tool, having passed through the latter.

The invention will be more readily understood with reference to the description which follows, in conjunction with the attached drawings in which:

FIG. 5 is a longitudinal sectional view of another embodiment of the implement of FIG. 1;

FIG. 6 is a cross sectional view of the de-scaling implement in FIG. 5 taken along line C—C;

Figure 1:
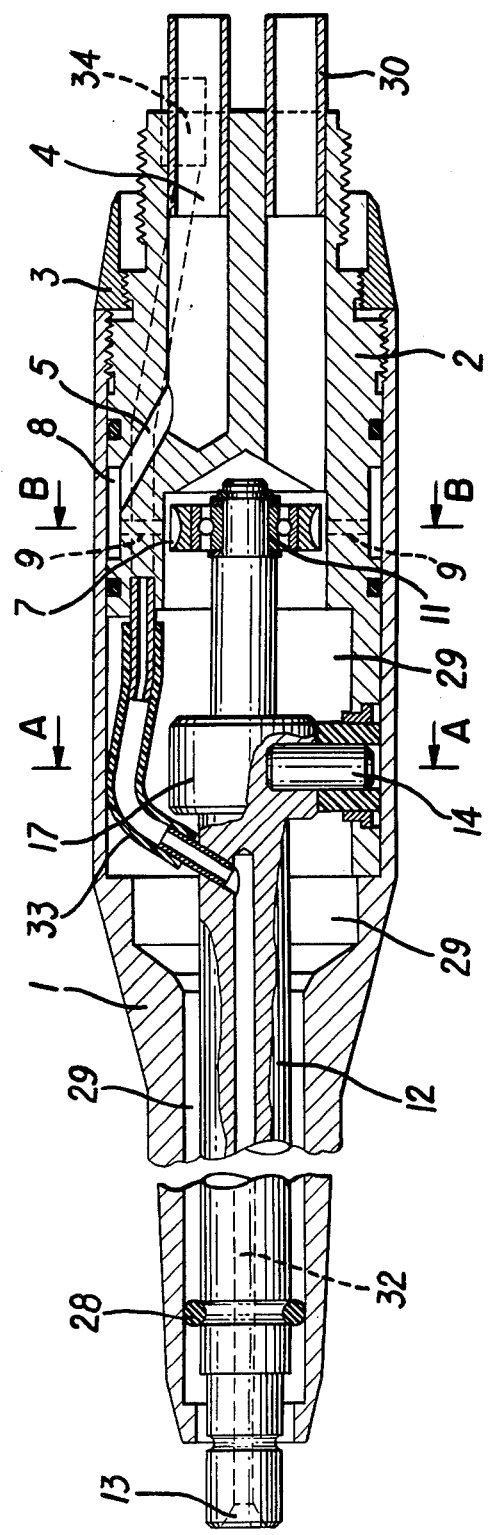
FIG. 1 is a longitudinal sectional view of a pneumatic de-scaling implement in accordance with the invention.

The de-scaling implement includes, in the conventional fashion, an elongated body (1) of conventional shape which will be familiar to the users of hand-held implements such as those used in dentistry for use with micro-motors.

A tubular body (2) is screwed into the inside of the rear portion of the body (1), this being immobilized in the body (1), in the conventional manner, using a counternut (3).

The pipes for introducing the compressed air and for supplying the rinsing water to the scaler tool are coupled up at a point on this tubular body (2) in the normal fashion for a dental tool driven by an air motor. A standardised four hole coupler is preferably used at this position.

The compressed air enters an axial passage (4) which is parallel to the axis of the body of the de-scaling implement. Then, via a branch passage (5), the air flow is deflected so as to be directed transversely, or substantially transversely, with respect to the body (1) of the de-scaling implement.

It then strikes the vanes (6) of a turbine or air motor (7). Preferably, the passage (5) discharges into an annular chamber (8) which includes a plurality of channels (9) which are directed so as to lead the air onto the turbine, and these channels are regularly distributed on the periphery of the annular chamber (8).

The turbine (7) is rotatably mounted on a ball bearing arrangement (10) in which the central race (11) is driven onto the end of a shaft (12) and is immobilized in the longitudinal sense on this shaft. The ball bearing arrangement may be replaced by a smooth bearing arrangement.

The structure and functions of the shaft (12) will now be described.

This shaft is unable to rotate and has the task of transmitting the vibratory movement which it is desired to obtain to the scaler tool carried on its end (13), such vibratory movement being produced by the turbine, and the structure of the latter will be described in greater detail below.

In order to prevent its being driven in rotation, the shaft (12) is immobilized, whilst however allowing it to perform vibratory motions, by pivots (14, 15, 16), these pivots being fixed, for example using a force fit arrangement, at one of their ends onto the shaft (12) at a position, for example, corresponding to that of the shoulder (17) having a diameter which is greater than the remainder of the shaft.

The purpose of these pivots, it will be recalled, is to maintain the shaft in a determined longitudinal position and consequently to prevent it rotating with respect to the tubular body (2).

Figure 2:
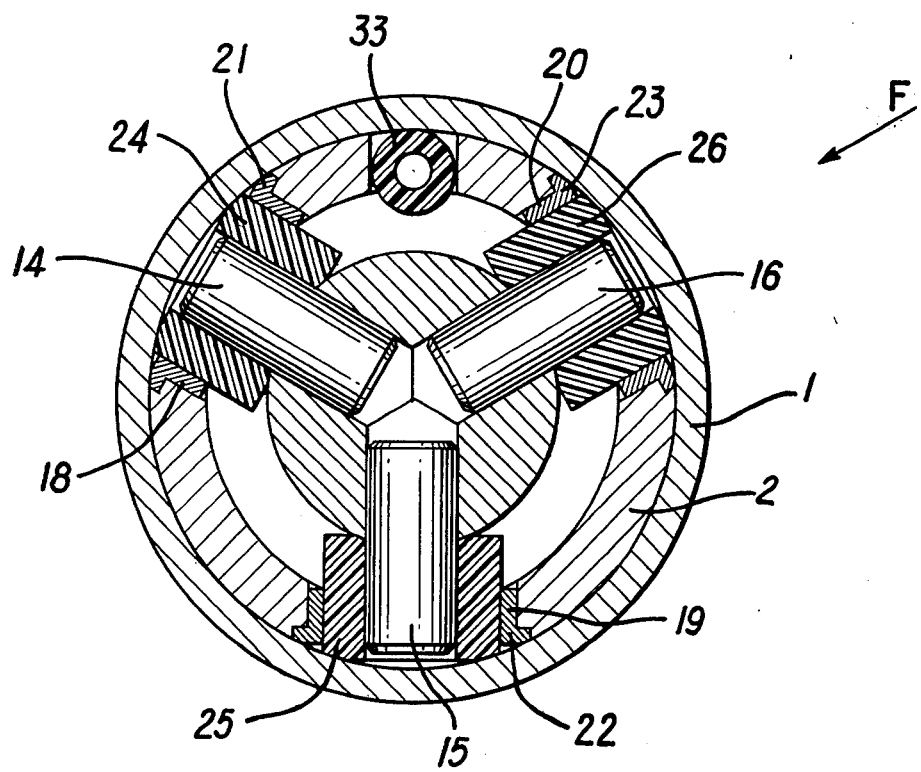
FIG. 2 is a cross sectional view of the de-scaling implement in FIG. 1 taken along line A—A.
Figure 3:
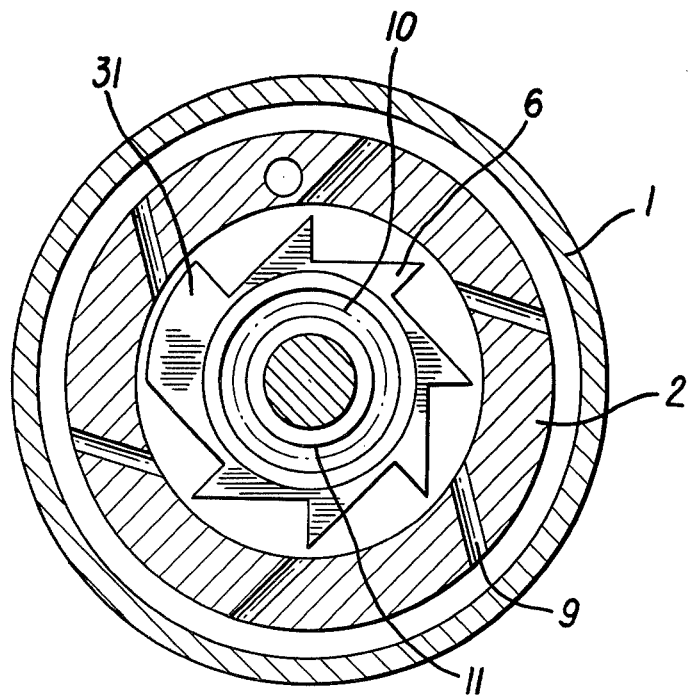
FIG. 3 is a cross sectional view of the de-scaling implement in FIG. 1 taken along line B—B.

In order to achieve this effect, three holes (18, 19, 20) are provided and these are regularly distributed over the periphery of the tubular body (2), as will be seen in FIG. 2. Rings (21, 22, 23) are engaged in these holes and each of these encircles a cushioning body (24, 25, 26) in an elastic material of the Silentbloc ® type, which are engaged by virtue of a loose frictional fit between the shouldered portion (17) of the shaft (12) and the internal wall of the body (1). The free ends of the pivots engage in these cushioning bodies.

Figure 4:
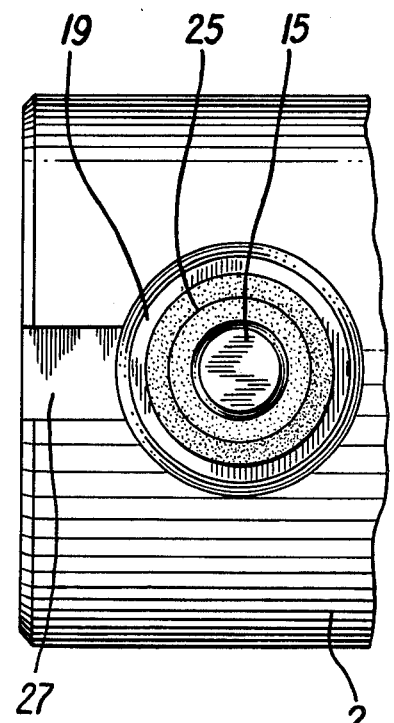
FIG. 4 is a view in the direction F in FIG. 2.

In order to carry out assembly of the implement, see FIG. 4, a number of grooves (27) are provided at the end of the tubular body (2) at the side which supports the pivots, and these are equal in number to the pivots in order to allow the passage of the latter. The rings (18, 19, 20) prevent the cushioning bodies (24, 25, 26) from overflowing into the said grooves (27).

Towards the front end of the shaft (12), sealing with regards to the outside of the implement is provided by using an annular seal (28) which thus defines a chamber (29) inside the de-scaling implement. This chamber (29) is in communication with the compressed air inlet (4, 5, 8, 9) and with an air outlet passage (30) provided at the rear end of the de-scaling implement, at the four hole coupler. After it has struck the vanes of the turbine (7), the air escapes into the chamber (29), where its further path is blocked at the forward end by the seal (28), so that it now passes out through the passage (30). This prevents the air from escaping at the forward end of the de-scaling implement, which is not conceivable from a practical point of view.

The vibrations are obtained from the turbine (7) by providing an out-of-balance mass (31) on the vaned wheel of the latter. It is only this eccentric mass which produces the vibrations.

The vibrations may vary in frequency and in amplitude as a function of various parameters such as:
eccentric mass of the turbine,
diameter of the turbine,
length of the shaft (12),
mass of the shaft (12),
position of the bearing points of the cushioning bodies (14,15,16),
degree of flexibility and position of the seal (28),
length of the special scaler tools.

By varying these various components, the vibration can be set at any desired value which is satisfactory to the operator.

The special scaler tools are held in position at the end (13) of the shaft (12) using any conventional means, for example using a screw or snap fitting arrangement etc., without this being in any manner limiting.

As has been stated above, it is equally important to be able to direct a cooling liquid, which will be generally water, to the position of the point of the scaler tool which tends to become heated up.

In order to achieve this, a conduit (32) for introducing the cooling liquid has been provided inside the shaft (12). The conduit (32) is connected by means of a flexible tube (33) arranged in the chamber (29), to the conduit (34) for introducing the fluid, which passes through the tubular body (2) and is connected up to the tube which carries the water from the supply arrangement. The flexible tube (33) is designed in such a way that it is neither subject to deterioration nor becomes detached as a result of the action of the vibrations of the shaft (12).

Reference is made now to FIGS. 5 and 6. For the common parts of this embodiment with the first one, the same reference numerals will be used.

At the end of the shaft (12), a sleeve (102) acting as a nut is screwed on a thread (101) of the shaft. This sleeve holds the outer ball-races of the bearings (103) and (104) in position.

A shaft (105) intergral with the turbine (7) is fitted on the inner ball-races of said bearings.

As the turbine rotates as described above, the inner ball-races rotate at the same speed. But the bearing-balls rotate at a speed which is two or three times lower, which increases their average life.

At last, the turbine (7) may also be unbalanced by a blade (106) having a hole (107).

We claim:

1. Implement for removing dental scale comprising, a hand-held tubular casing, a rigid shaft extending axially in said casing for mounting externally of the casing a dental scale-removing tool on a free end thereof, means for mounting the shaft internally of the casing to restrain it from rotation and allowing it to vibrate rotationally, a fluid-driven dynamically unbalanced motor coupled to the shaft for rotation about an axis parallel to the longitudinal axis of the shaft to impart to the shaft subsonic rotational vibrations, a bearing coupling the motor to said shaft for rotation about said axis, and the shaft being sufficiently rigid to vibrate free of torsion.

2. Implement for removing dental scale according to claim 1, in which said motor comprises an air-driven turbine having a rotor provided with a mass thereon dynamically unbalancing the rotor so that it develops said vibrations, and said bearing coupling the rotor to said shaft for transmitting said vibrations thereto.

3. Implement for removing dental scale according to claim 1, in which said motor comprises an air-driven turbine having a rotor with rotor blades one of which is constructed to dynamically unbalance the rotor so that it develops said vibrations, and said bearing coupling the rotor to said shaft for transmitting said vibrations thereto.

4. Implement for removing dental scale according to claim 1, in which said fluid-driven motor comprises an air-driven turbine having a dynamically unbalanced rotor for developing said vibrations, said bearing coupling the rotor to said shaft for transmitting said vibrations thereto, said housing having means therein defining air-supply and air-discharge ducts for supplying air to the turbine and discharging it from the housing, and means in said housing for supplying cooling water to the scale-removing tool for maintaining it cooled during use.

5. Implement for removing dental scale comprising, a hand-held tubular casing, a rigid shaft extending axially in said casing for mounting externally of the casing a dental scale-removing tool on a free end thereof, means for mounting the shaft internally of the casing to restrain it from rotating and allowing it to vibrate rotationally, a fluid-driven dynamically unbalanced motor coupled to the shaft to impart to the shaft subsonic rotational vibrations, the shaft being sufficiently rigid to vibrate free of torsion, said means for mounting the shaft internally of the casing to restrain it from rotating comprising a plurality of pivots extending radially from said shaft, and resilient restraining means restraining the pivots from moving rotationally and axially.

* * * * *